(12) United States Patent
Berghaus

(10) Patent No.: US 6,383,207 B1
(45) Date of Patent: *May 7, 2002

(54) MEDICAL INSTRUMENT FOR USE IN RHINOPLASTY

(75) Inventor: Alexander Berghaus, Berlin (DE)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/578,734

(22) Filed: May 25, 2000

Related U.S. Application Data

(63) Continuation of application No. PCT/EP99/09487, filed on Dec. 3, 1999.

(30) Foreign Application Priority Data

Apr. 6, 1999 (DE) .......................................... 199 17 287

(51) Int. Cl.⁷ .................................................. A61F 5/08
(52) U.S. Cl. ................................................. 606/204.45
(58) Field of Search ........................... 606/204.45, 210, 606/211, 199; 600/213, 214; 602/17, 6, 5, 12; 294/99.2

(56) References Cited

U.S. PATENT DOCUMENTS

| | | | | |
|---|---|---|---|---|
| 2,509,157 A | * | 5/1950 | Lind | 602/17 |
| D233,398 S | * | 10/1974 | Lee | 294/99.2 |
| 4,457,756 A | * | 7/1984 | Kern et al. | 606/210 |
| 4,787,663 A | * | 11/1988 | Laramie | 294/99.2 |
| D343,096 S | * | 1/1994 | Lachapelle | 294/99.2 |
| 5,334,215 A | * | 8/1994 | Chen | 606/210 |

FOREIGN PATENT DOCUMENTS

WO  WO93/12701  *  7/1993  ................. 294/99.2

* cited by examiner

Primary Examiner—David O. Reip
Assistant Examiner—Julian W. Woo
(74) Attorney, Agent, or Firm—St. Onge Steward Johnston & Reens LLC.

(57) ABSTRACT

A medical instrument for use in rhinoplasty has a first rod-shaped element that comprises a distal portion intended to hold nasal cartilage of a nose side. The instrument further comprises a second rod-shaped element having a distal portion for holding nasal cartilage of the other side of the nose, there being provided a fixing element which is detachably mounted on the first element and the second element and which mutually fixes the two elements one beside the other in approximately parallel alignment one relative to the other.

12 Claims, 2 Drawing Sheets

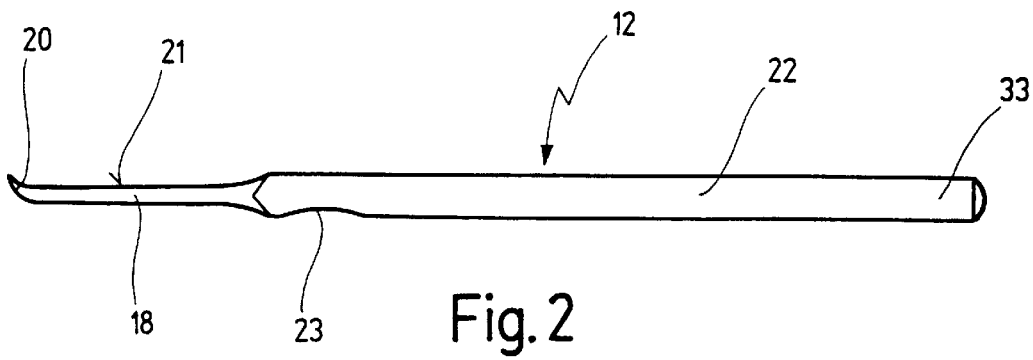
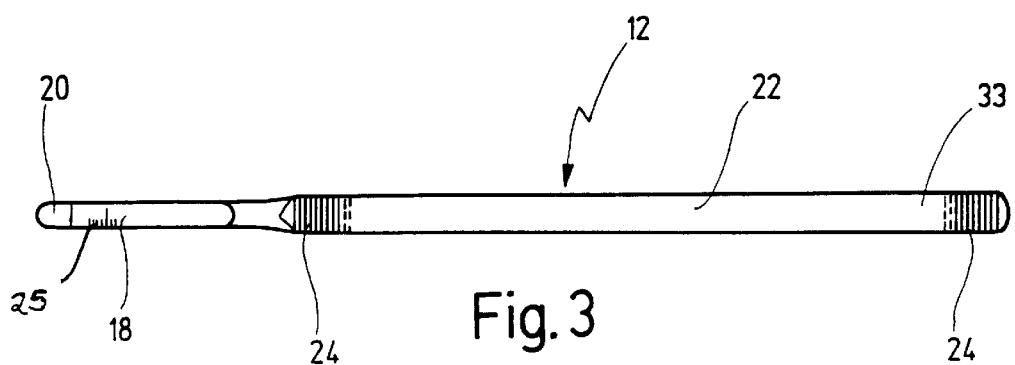
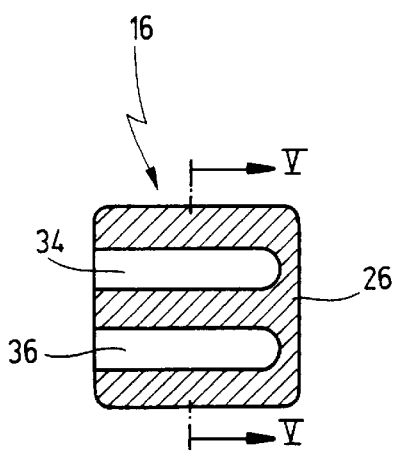
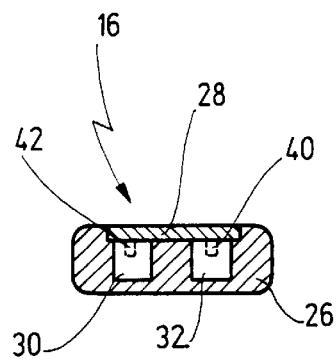
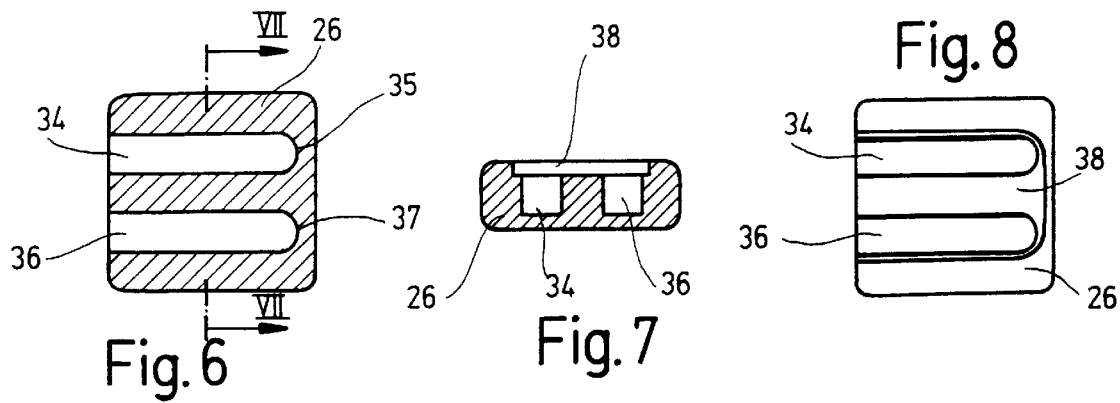

MEDICAL INSTRUMENT FOR USE IN RHINOPLASTY

CROSS-REFERENCE TO PENDING APPLICATION

This application is continuation of pending International application PCT/EP 99/09487 filed Nov. 3, 1999.

BACKGROUND OF THE INVENTION

The present invention relates to a medical instrument for use in rhinoplasty having a first rod-shaped element that comprises a distal portion intended to hold nasal cartilage of a nose side.

An instrument of this kind has been known, for example, from the German company catalogue of Karl Storz GmbH & Co., Tuttlingen, entitled "STORZ—Karl Storz-Endoskope", Vol. "Endoskope und Instrumente für HNO" (endoscopes and instruments for ENT), $5^{th}$ edition, 1996, page N 15 A.

Such an instrument is used in the field of rhinoplasty. In rhinoplasty, the structure of the nose is transformed, under functional and esthetic aspects, for example to reduce the size of the nose by manipulation of the nasal cartilage, or for removing any deformities, for example on the tip of the nose or the sides of the nose.

To permit corresponding operation on the nasal cartilage of both sides, for example, the latter must be completely exposed and presented in clearly visible form in order to permit the in part "filigree" manipulations to be carried out on these elements. For this purpose, one initially makes a cut in the nasal cartilage, without, however, completely cutting off the nasal cartilage. Thereafter, the nasal cartilage must be pulled clear of the nasal cavity of the respective half of the nose, in order to be cleaned from any skin tissue and soft tissue. To permit the desired manipulations to be carried out on the nasal cartilage now exposed, the latter must be held in stationary condition in this advanced position in the area in front of the nostril.

The German company catalogue mentioned before shows under instrument number 478303 a rod-shaped element similar to a splint, which is suited for grasping by its distal end the nasal cartilage of one half of the nose, for pulling it out from the respective nasal cavity and for holding the nasal cartilage in that pulled-out position, for which purpose the nasal cartilage is loaded onto the level distal portion of the rod-shaped element. This is achieved by pushing the distal portion of the rod-shaped element below the nasal cartilage still supported in the nasal cavity.

However, this known instrument permits only one nasal cartilage to be held in the pulled-out position so that the nasal cartilage of the left and the right halves of the nose must be worked one after the other.

It is, however, of decisive importance for the success of any rhinoplasty measure that simultaneous and symmetrical working of the nasal cartilage of both sides must be possible, i.e. that the nasal cartilage of both sides must be exposed and presented in clearly visible fashion one beside the other, in order to permit the surgeon to compare the nasal cartilage of both sides continuously during the operation.

Now, in order to permit the nasal cartilage of both sides to be held in the pulled-out position one beside the other, one might consider to use two of the known instruments, one for the nasal cartilage of the left half of the nose, and one for the nasal cartilage of the right half of the nose. However, this would present the problem that both rod-shaped elements would have to be held by the surgeon or by an assistant, which would hinder the surgeon in his work, namely the manipulation of the nasal cartilage. Thus, the simultaneous use of two of the known instruments proves to be disadvantageous under aspects of maneuverability of such an instrument.

Now, it is the object of the present invention to improve an instrument of the before-mentioned kind and to provide a methode for presenting nasal cartilage so that it will be rendered possible to simultaneously present the nasal cartilage of both the left and the right halves of the nose with the aid of the instrument, which in addition can be handled with ease.

SUMMARY OF THE INVENTION

The invention solves this object with respect to the before-mentioned instrument by the fact that the instrument comprises a second rod-shaped element having a distal portion for holding nasal cartilage of the other side of the nose, and a fixing element which is detachably mounted on the first element and the second element and which mutually fixes the two elements one beside the other in approximately parallel alignment one relative to the other.

By providing two rod-shaped elements both the nasal cartilage of the left half of the nose and the nasal cartilage of the rigth half of the nose can now be simultaneously held in the pulled-out position one beside the other, whereby the nasal cartilage of both sides can be presented in clearly visible fashion so as to permit the surgeon to constantly compare the nasal cartilage of both sides during his manipulations on the nasal cartilage. The fixing element provided according to the invention now presents the particular advantage that the two rod-shaped elements, each of which supports the nasal cartilage of one side, can be fixed in position one relative to the other so that during operation, which usually is carried out with the patient lying on his back, two rod-shaped elements, being fixed by means of the fixing element, can be positioned, for example, on the patient's chin or on a respiration mask. Thus, it is not necessary that the two rod-shaped elements be held by the surgeon or an assistant during the manipulations on the nasal cartilage, since the fixing element ensures that the two elements are sufficiently fixed in their positions. The surgeon, therefore, has his two hands free for carrying out the required manipulations on the nasal cartilage of both sides, and is not hindered by the close presence of an assistant, either. The fact that the fixing element can be mounted detachably on the first and the second elements provides the additional advantage that the first rod-shaped element can be separately used, with the fixing element initially detached, for picking up and pulling out the nasal cartilage, for example of the left half of the nose, whereafter the second rod-shaped element can be used separately in order to pick up and pull out the nasal cartilage of the right half of the nose, which operations can be carried out more easily with individual separate rod-shaped elements as provided herein according to a method for simultaneously presenting nasal cartilage of a left and a right half of a nose, according to the invention. Once the nasal cartilage of both sides has been loaded onto the respective rod-shaped elements, the two rod-shaped elements are fixed in their position one relative to the other by mounting the fixing element, whereafter the instrument can be deposited on the patient's face, as mentioned before, with the nasal cartilage of both sides presented in clearly visible form for manipulation. Thus, handling of the instrument according to the invention is especially easy. Making the fixing element detachable provides the additional advantage that the rod-shaped elements can be used without the fixing element also for different purposes.

The object underlying the present invention is thus perfectly achieved.

According to a preferred embodiment, the distal portion of the first element and the distal portion of the second element are configured symmetrically one relative to the other.

This feature provides the advantage that the symmetrical presentation of the nasal cartilage of both sides is rendered possible, in connection with the fixing block, which further facilitates the symmetrical treatment of the nasal cartilage of both sides, which is so desirable for the success of the plastic operation.

In a further preferred embodiment the distal portion of the first element and the distal portion of the second element are provided on their upper surfaces with markings for improved orientation.

This feature provides the advantage that the markings, being constituted for example by a millimeter scale, permit the dimensions of the nasal cartilage of both sides to be compared more precisely, whereby precise symmetrical working of the nasal cartilage of both sides is guaranteed.

According to a preferred embodiment the fixing element is configured as a slip-on element that can be fitted from the proximal end of the elements.

This provides advantageously a connecting mechanism between the fixing elements and the rod-shaped elements that can be handled with special ease when the two rod-shaped elements are to be fixed one to the other after the nasal cartilage of both sides has been loaded on the respective elements. Sliding the fixing element onto the elements from their proximal ends provides the advantage that no forces acting transversely to the longitudinal direction of the elements must be applied when mounting the fixing element, which ensures that no undesirable leverage is exerted upon the loaded nasal cartilage of both sides by the rod-shaped elements being moved out of their orientation along their longitudinal axes.

It is further preferred in this connection if the fixing element has two longitudinally extending openings intended to receive proximal longitudinal portions of the elements.

It is an advantage of this arrangement that the fixing element embraces the proximal ends of the two rod-shaped elements over portions extending in longitudinal direction, whereby the two elements are fixed in position one beside the other with particular stability so that any tilting of the two elements out of their approximately parallel orientation one relative to the other is avoided.

It is further preferred in this connection if the fixing element comprises a block member in which the openings are provided in the form of grooves, the fixing element further comprising a cover that closes the grooves along their open long side.

This two-part embodiment of the fixing element is especially advantageous under aspects of manufacture since the grooves can be produced in the block member by a milling process. This allows the openings in the fixing element to be given a non-circular cross-portion, if desired, in order to allow the two elements to be positively received in case their proximal end portions also exhibit a non-circular cross-portion. The cover then advantageously closes the grooves along their open long sides so that the openings are laterally closed on all sides and safe fixing of the fixing element to the two elements is rendered possible.

The cover may be fixed to the block member, for example by welding. However, it is also preferred if the cover is detachably mounted on the block member.

This provides the advantage that any dirt gathering in the openings can be removed more easily with the cover detached, with improves the cleaning properties of the fixing element. In addition, this further provides the advantage that in case the elements should get canted in the fixing element so that they can no longer be easily withdrawn from the fixing element, the elements can be removed more easily after removal of the cover. The cover may be detachably mounted on the block member, for example by means of screws or by a snap-on arrangement.

According to a further preferred embodiment, the fixing element is configured as a slip-on element that can be slipped or slid onto the elements from a lateral side.

This, too, presents an advantageous solution for a connecting mechanism for mounting the fixing element on the two elements.

According to a further preferred embodiment, the fixing element can be mounted on the elements in a self-locking fashion.

It is an advantage of this arrangement that no additional measures, such as screws of the like, are required for mounting the fixing element on the two rod-shaped elements. In the case of the before-mentioned embodiment, where the fixing element is configured as a slip-on element that can be fitted from the proximal end, this may be realized for example by an elastic element, for example in the form of a bent leaf spring that locks the proximal longitudinal portions of the two rod-shaped elements in the openings by a clamping effect.

It is further preferred in this connection if the fixing element can be snap-locked on the two elements.

This also leads to an arrangement for fixing the fixing element on the two rod-shaped elements that can be handled with special ease, for example by providing an elastic detent in the openings of the fixing element, which snaps into a locking groove provided in the longitudinal portions of the two rod-shaped elements, received in the openings, when mounting the fixing element.

Further advantages are evident from the description and from the appended drawings.

It is understood that the features recited above and those yet to be explained below can be used not only in the respective combinations indicated, but also in other combinations or in isolation, without leaving the context of the present invention.

BRIEF DESCRIPTION OF THE DRAWINGS

An exemplary embodiment of the invention is shown in the drawings and will be explained in more detail in the description below.

In the drawings:

FIG. 2 shows a side view of an isolated rod-shaped element of the instrument of FIG. 1;

FIG. 3 shows a top view of the instrument of FIG. 1;

FIG. 4 shows a horizontal longitudinal portion through a fixing element of the instrument of FIG. 1;

FIG. 5 shows a portion, taken along line V—V in FIG. 4, of the fixing element of FIG. 4;

FIG. 6 shows a portion corresponding to FIG. 4 through a block member of the fixing element;

FIG. 7 shows a portion, taken long line VII—VII in FIG. 6, of the block member of FIG. 6;

FIG. 8 shows a top view of the block member of FIG. 6; and

DETAILED DESCRIPTION OF A PREFERRED EMBODIMENT

Figure 1:
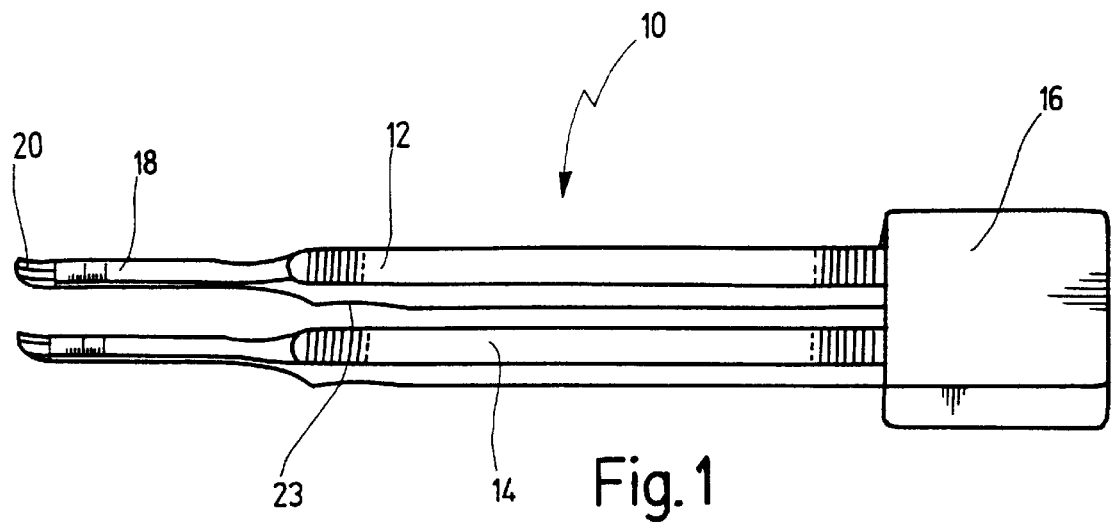
FIG. 1 shows a perspective view of an instrument according to the invention in assembled condition.

FIG. 1 shows a medical instrument, indicated generally by reference numeral 10, that is used in rhinoplasty for surgical transformation of the structure of a nose, as will be described in more detail hereafter with reference to FIG. 9.

Instrument 10 comprises a first rod-shaped element 12 and a second rod-shaped element 14.

First rod-shaped element 12 and second rod-shaped element 14 are fixed one to the other in approximately parallel orientation one beside the other, by means of a fixing element 16. Fixing element 16 is detachably mounted on elements 12 and 14. Elements 12 and 14, and fixing element 16, are made from a steel grade suited for medical purposes.

Referring to FIGS. 2 and 3, the configuration of first rod-shaped element 12 will now be described in more detail, it being noted that the configuration of second rod-shaped element 14 is identical to the configuration of first rod-shaped element 12.

Rod-shaped element 12 comprises a distal portion 18 whose outer distal point 20 is slightly curved relative to the longitudinal axis of rod-shaped element 12. Distal portion 18 of rod-shaped element 12 serves to hold the nasal cartilage of one half of the nose, for which purpose the latter is loaded onto its upper surface 21, which exhibits a level planar configuration, point 20, being curved toward the upper surface 21, preventing the nasal cartilage from slipping off the surface. Distal portion 18 of rod-shaped element 12 has a semi-circular cross-portion and is made from solid material, which means that a lower surface, opposite to upper surface 21, exhibits a circular shape.

On its upper surface 21, distal portion 18 is provided with an orientation marking 25 which serves, together with a corresponding marking on the distal portion of element 14, as a standard of comparison during operation of the nasal cartilage of the two sides of the nose. Such a marking 25 may have the form of a millimeter scale with corresponding lines provided on upper surface 21.

Distal portion 18 of rod-shaped element 12 is followed by an element body 22, likewise made from solid material but having a rectangular cross-portion.

A cradle-like recess 23 provided on the lower surface of element body 22, adjacent distal portion 18, allows ergonomic handling of element 12.

Both the lower surface and the opposite upper surface of the element body 22 are provided with a full-length axial corrugation 24 that improves the grip of rod-shaped element 12 when handling the latter. In FIG. 3, corrugation 24 is not shown over its full length, in order to simplify the representation.

Rod-shaped elements 12 and 14 are configured in the way of splints or chisel-like instruments, and distal point 20 on distal end 18 may also have a sharpened distal end, for example for performing a scraping or cutting function.

In addition, distal portion 18 of element 12, and the corresponding portion of element 14, are configured symmetrically one relative to the other.

In FIGS. 4 to 8 fixing element 16 is shown in more detail.

Fixing element 16 generally has a two-part design. Fixing element 16 comprises a block member 26 and a cover 28.

Fixing element 16 comprises a first opening 30 and a second opening 32, each of rectangular cross-portion, whose cross-portional surfaces are slightly larger than the cross-portional surface of element body 22 of rod-shaped element 12 and the corresponding element body of second rod-shaped element 14, respectively, so that the approximately longitudinal portions 33 of rod-shaped element 12 and 14, respectively, are positively received in openings 30 and 32 when fixing element 16 is mounted on elements 12 and 14.

Openings 30 and 32 are configured as grooves 34 and 36 in block member 26 of fixing element 16, and extend over almost the full length of block member 26, a proximal end 35 of groove 36 and a proximal end 37 of groove 36 being closed. Grooves 34 and 36 are milled into block member 26 during manufacture thereof.

Cover 28 closes the open side of grooves 34 and 36 so that openings 30 and 32 are laterally closed on all sides, with only their distal ends remaining open. Cover 28 is positively fitted in a recess 38 in the block member 26 so that fixing element 16 exhibits a smooth surface, free from any steps, and generally the shape of a flat cuboid.

Cover 28 is fixed to block member 26 by welding, bonding, or the like.

However, cover 28 may also be detachably connected with block member 26, for example by means of screws or a snap-on mechanism so that cover 28 can be detached from block member 26 as required, for example for cleaning of fixing element 16.

In the embodiment described above, fixing element 16 is configured as a slip-on element that can be slid onto rod-shaped element 12 or rod-shaped element 14, respectively, from the proximal end.

In a different embodiment, not shown in the drawing, the fixing element may, however, be configured as a slip-on element that can be fitted or snapped onto rod-shaped elements 12 and 14 from a lateral side. Fixing element 16 may, for example, be used also without cover 28, in which case block member 26, with the laterally open grooves 34 and 36, can be used as fixing element to be snapped on from the side, for which purpose corresponding locking means may be additionally provided in grooves 34 and 36 so that block member 26 can then be safely fixed on rod-shaped elements 12 and 14, even without cover 28.

Further, fixing element 16 can be mounted in a self-locking fashion on rod-shaped elements 12 and 14. FIG. 5 shows in this connection, diagrammatically and in dashed lines, an elastic element 40 arranged in opening 32 and an elastic element 42 arranged in opening 30, which may be configured, for example, as leaf springs fixed on cover 28, for clamping the proximal longitudinal portions 33 of rod-shaped elements 12 and 14 in openings 30 and 32.

Further, locking means—not shown—may be provided on fixing element 16 in openings 30 and 32, for example in the form of detents coacting in locking fashion with corresponding notches in the proximal longitudinal portions or with corrugation 24.

Figure 9:
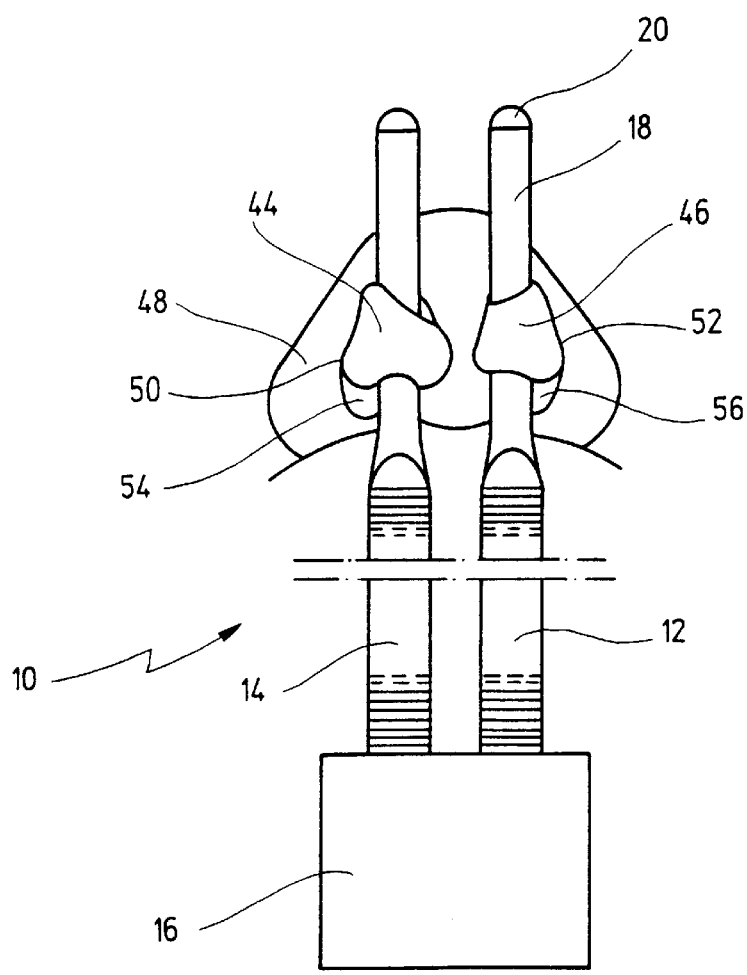
FIG. 9 shows a diagrammatic representation of the function of the instrument used in rhinoplasty.

Referring to FIG. 9, the function of instrument 10 will now be described in more detail with reference to its use in rhinoplasty for presenting the nasal cartilage of both sides of a nose.

In FIG. 9, a nose is indicated by reference numeral 48, the nasal cartilage of the right half of the nose is indicated by reference numeral 44, and the nasal cartilage of the left half of the nose is indicated by reference numerals 46.

In order to be able to present nasal cartilages 44 and 46, as illustrated in FIG. 9, nasal cartilages 44 and 46 has been separated in part by partial cuts made with the aid of other suitable instruments. Nasal cartilages 44, 46 were, however, not cut off completely but are still connected, at a connection point 50 or 52, respectively, with the remaining cartilage in the respective nasal cavity. The cuts are applied in such a way that nasal cartilages 44 and 46 of both sides can be pulled or folded out through nostrils 54 and 56.

For pulling out and, thus, presenting nasal cartilages 44 and 46 of both sides, one now makes use of instrument 10.

With fixing element 16 initially removed, one first grips nasal cartilage 46 of the left side in its nasal cavity in nostril 56, for example with the aid of rod-shaped element 12, by slipping distal portion 18 with its point 20 below nasal cartilage 46, that has been cut off in part, and pulling out the latter through nostril 56. Once nasal cartilage 46 has been pulled out through nostril 56, distal portion 18 is positioned in front of nostril 56, as shown in FIG. 9, so that nasal cartilage 46 is prevented from folding back into the left nasal cavity. Nasal cartilage 46 is, thus, properly presented.

During the step that follows, second rod-shaped element 14 is used to proceed in the same fashion with nasal cartilage 44 of the right side, until the latter has likewise been pulled out from the nasal cavity and is presented in clearly visible fashion.

Thereafter, fixing element 16 is slid onto rod-shaped elements 12 and 14 from their proximal ends, whereby elements 12 and 14 are fixed one to the other in their position in parallel orientation one relative to the other, at a spacing corresponding approximately to the spacing of nostrils 54 and 56.

The arrangement forming instrument 10 and comprising rod-shaped element 12, rod-shaped element 14 and fixing element 16, now forms a rigid unit that can be positioned on the patient's face, with the fixing element 16 resting approximately on the patient's chin. The surgeon can then carry out the necessary manipulations, i.e. apply the necessary modifications to nasal cartilages 44 and 46, without any need for the instrument 10 to be held by the surgeon himself or by an assistant. Thus, instrument 10 permits nasal cartilages 44 and 46 of both sides to be presented and treated symmetrically, one beside the other.

What I claim is:

1. Medical instrument for use in rhinoplasty, comprising:
    a first rod-shaped element having a distal portion intended to hold nasal cartilage of a nose side and a proximal longitudinal portion;
    a second rod-shaped element having a distal portion for holding nasal cartilage of the other side of the nose and a proximal longitudinal portion;
    a rigid fixing element which is detachably mounted on said first element and said second element and which mutually and immovably fixes said first and second rod-shaped elements one beside the other in approximately parallel alignment one relative to the other, said rigid fixing element having elongated recesses for receiving the proximal longitudinal portions of said first and second rod-shaped elements.

2. The instrument of claim 1, wherein said distal portion of said first element and said distal portion of said second element are configured symmetrically one relative to the other.

3. The instrument of claim 1, wherein said distal portion of said first element and said distal portion of said second element are provided on their upper surfaces with markings for improved orientation.

4. The instrument of claim 1, wherein said fixing element is configured as a slip-on element that can be fitted from proximal ends of said first and second elements.

5. The instrument of claim 4, wherein said elongated recesses are two longitudinally extending openings intended to receive the proximal longitudinal portions of said first and second elements.

6. The instrument of claim 5, wherein said fixing element comprises a block member in which said openings are provided in the form of grooves, said fixing element further comprising a cover that closes said grooves along their open long side.

7. The instrument of claim 6, wherein said cover is detachably mounted on said block member.

8. The instrument of claim 1, wherein said fixing element is configured as a slip-on element that can be slipped or slid onto the elements from a lateral side.

9. The instrument of claim 1, wherein said fixing element can be mounted on said first and second elements in a self locking fashion.

10. The instrument of claim 9, wherein said fixing element can be snap-locked on said first and second elements (12, 14).

11. Medical instrument for use in rhinoplasty, comprising:
    a first rod-shaped element having a longitudinal proximal portion and a distal portion intended to hold nasal cartilage of a nose side;
    a second rod-shaped element having a longitudinal proximal portion and a distal portion for holding nasal cartilage of the other side of the nose;
    a fixing element having a block member provided with two longitudinally extending grooves which removably receive the proximal portions of the first and second rod-shaped elements, respectively, to have said first and second rod-shaped elements mutually fixed one beside the other in approximately parallel alignment one relative to the other, and a cover closing said grooves along their open long sides.

12. Medical instrument defined in claim 11, wherein said cover is detachably mounted on said block member.

* * * * *

UNITED STATES PATENT AND TRADEMARK OFFICE
CERTIFICATE OF CORRECTION

PATENT NO.    : 6,383,207 B1 Page 1 of 1
DATED         : May 7, 2002
INVENTOR(S)   : Alexander Berghaus It is certified that error appears in the above-identified patent and that said Letters Patent is hereby corrected as shown below:

<u>Title page,</u>
Item [30], should read as follows:

-- [30]  Foreign Application Priority Data

April 16, 1999    DE    199 17 287 --

Signed and Sealed this

Seventeenth Day of September, 2002

Attest:

Attesting Officer

JAMES E. ROGAN
*Director of the United States Patent and Trademark Office*